United States Patent [19]

Telfair et al.

[11] Patent Number: 4,911,711
[45] Date of Patent: Mar. 27, 1990

[54] SCULPTURE APPARATUS FOR CORRECTING CURVATURE OF THE CORNEA

[75] Inventors: William B. Telfair, Newtown; Paul R. Yoder, Jr., Wilton; Clifford A. Martin, Bridgeport, all of Conn.; Francis A. L'Esperance, Jr., Englewood, N.J.

[73] Assignee: Taunton Technologies, Inc., Monroe, Conn.

[21] Appl. No.: 938,633

[22] Filed: Dec. 5, 1986

[51] Int. Cl.$^4$ .............................................. A61M 5/06
[52] U.S. Cl. ......................................... 606/5; 606/11; 219/121.6; 219/121.68; 219/121.75; 219/121.83
[58] Field of Search ..................... 128/303.1, 362, 395; 219/121 L, 121 LA, 121 LB, 121 LG, 121 LP, 121 LQ, 121 LU, 121 LX, 121 LZ, 121.6–121.62, 121.64, 121.68, 121.73, 121.74, 121.75, 121.78, 121.8, 121.83; 350/174; 606/5, 11, 12

[56] References Cited

U.S. PATENT DOCUMENTS

| | | | |
|---|---|---|---|
| 3,348,547 | 10/1967 | Kavanagh | 128/303.1 |
| 3,703,176 | 11/1972 | Vassiliadis et al. | 128/303.1 |
| 3,705,758 | 12/1972 | Haskal | 219/121 LR |
| 3,941,973 | 3/1976 | Luck, Jr. et al. | 219/121 LR |
| 4,315,130 | 2/1982 | Inagaki et al. | 219/121 LR |
| 4,370,026 | 1/1983 | Dubroeucq | 350/174 |
| 4,370,540 | 1/1983 | Davis et al. | 219/121 L |
| 4,518,232 | 5/1985 | Dagenais | 219/121 LQ |
| 4,545,651 | 10/1985 | Kato et al. | 350/174 |
| 4,551,608 | 11/1985 | Opower | 219/121 LQ |
| 4,633,873 | 1/1987 | Chaffee et al. | 128/303.1 |
| 4,648,400 | 3/1987 | Schneider et al. | 128/303.1 |
| 4,669,466 | 6/1987 | L'Esperance | 128/395 |
| 4,702,245 | 10/1987 | Schröder et al. | 128/303.1 |
| 4,719,912 | 1/1988 | Weinberg | 128/303.1 |
| 4,724,522 | 2/1988 | Belgorod | 128/303.1 |
| 4,729,372 | 3/1988 | L'Esperance, Jr. | 128/395 |
| 4,732,148 | 3/1988 | L'Esperance, Jr. | 128/395 |

FOREIGN PATENT DOCUMENTS 163589 9/1983 Japan .......................... 219/121 LE

OTHER PUBLICATIONS

"Response of the Corneal Epithelium to KrF Excimer Laser Pulses" by Taboda et al.; Health Physics, vol. 40, May, 1981, pp. 677–683.
"Excimer Laser Surgery of the Cornea" by Trokel et al.; Am. J. Ophthal., vol. 96, No. 6, Dec., 1983, pp. 710–715.

Primary Examiner—Lee S. Cohen
Assistant Examiner—David Shay
Attorney, Agent, or Firm—Hopgood, Calimafde, Kalil, Blaustein & Judlowe

[57] ABSTRACT

In the context of ultraviolet-laser sculpting of the cornea to achieve optical correction through a newly shaped anterior surface, the invention subjects the laser beam to certain shaping and homogenizing operations prior to any attempt to specially characterize the beam for a particular sculpturing procedure. In a preferred embodiment, the shaping and homogenizing operations present a tolerably homogeneous beam of enlarged dimension, so that specialty-characterizing may proceed on a dimensional scale that is greater than the corresponding dimension of ultimate surgical delivery to the eye, thereby enabling greater control of the quality of specialty-characterizing. Provision is made for selectively monitoring the quality of the homogeneity and/or of the specially-characterized beam, with further provision for automated cutoff of laser beam delivery to an eye in the event that quality is not within predetermined limits of tolerance. And preferably, all beam shaping, homogenizing and characterizing operations proceed in a controlled environment which precludes ozone development and thus minimizes the beam-degrading effect of ozone and particulates or other contaminants.

26 Claims, 3 Drawing Sheets

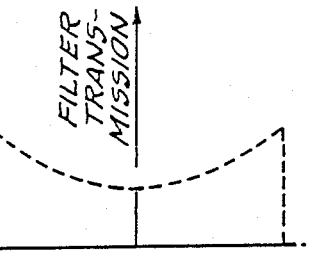
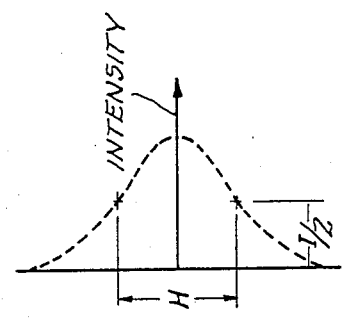
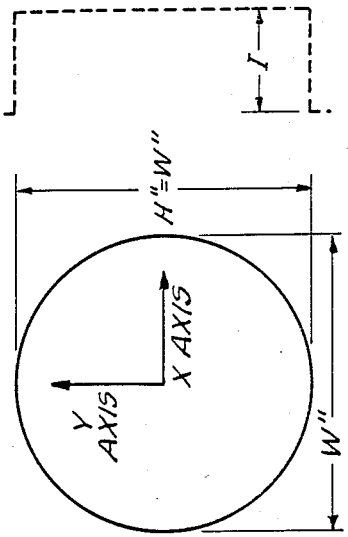
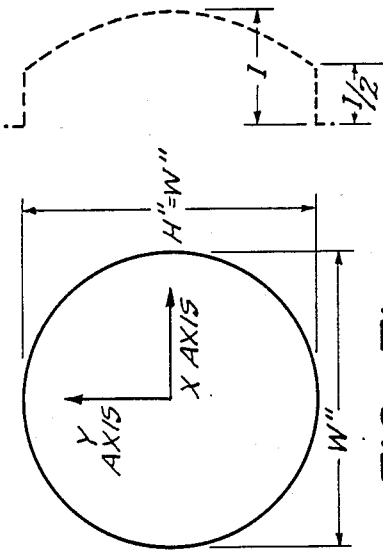
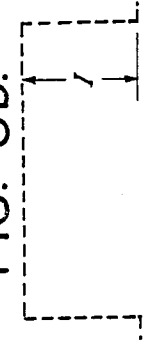
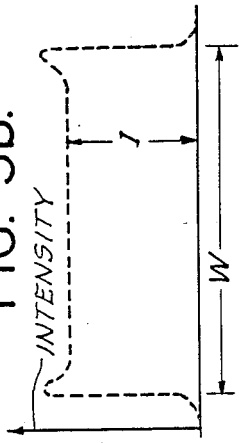
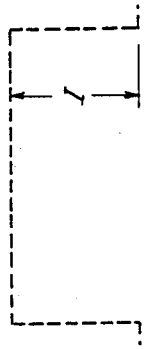

SCULPTURE APPARATUS FOR CORRECTING CURVATURE OF THE CORNEA

BACKGROUND OF THE INVENTION

The invention relates to that aspect of ophthalmic surgery which is concerned with laser operations upon the external surface of the cornea, such operations involving controlled ablation of the cornea with penetration into the stroma and volumetric removal of corneal tissue whereby said external surface is characterized by a sculptured new curvature having improved optical properties.

Several different techniques and related apparatus are described for such sculpture of the cornea, in pending L'Esperance patent applications, including Ser. No. 748,358, (now U.S. Pat. No. 4,665,913) Ser. No. 691,923, (now U.S. Pat. No. 4,669,466) Ser. No. 891,169, and Ser. No. 891,285, (now U.S. Pat. No. 4,732,148) and reference is made to these patent applications for greater detail. Suffice it to say that these techniques rely on ultraviolet radiation which is preferably of less than 200-nm wavelength, as is provided by an excimer laser operating with argon fluoride Typical beam dimensions of the excimer laser are rectangular, and said Ser. No. 891,169 discloses a circular opening in a mask for reducing the laser beam to a cylinder of circular section; thereafter, the cylindrical beam is variously characterized so that at incidence with the cornea and on the eye axis, the distribution of laser-flux density will be a correspondingly distributed pattern of cornea-curvature correction.

In said Ser. No. 891,285, the sculpturing result for cornea-curvature correction is achieved by exposing the cornea to a sequence of mask openings, of different but related areas, whereby the cumulative effect is to so expose certain areas more in relation to others that the consequence is the desired net curvature change.

The techniques of both said applications Ser. No. 891,169 and Ser. No. 891,285 involve non-scanning use of the involved laser beam, and they assume that a sufficiently homogenous beam will be available prior to characterizing the same for sculpturing delivery to the cornea. But we have found that the flux-density distribution within such a beam is not necessarily uniform and that it can vary with time, thus presenting the possibility of impaired quality of the intended curvature correction. The present invention addresses this specific problem.

BRIEF STATEMENT OF THE INVENTION

It is an object of the invention to provide a method and means for improving the quality of laser-sculpted curvature correction of the cornea.

It is a specific object to achieve the above object by improving the homogeneity of laser-flux distribution prior to characterizing the distribution for specific different curvature-correction purposes.

It is also a specific object to improve the quality of characterized laser radiation delivered for corneal surgery.

Another specific object is to achieve the above objects with means for monitoring flux distribution to determine its acceptability vel non for the intended surgical purpose.

A still further object is to provide means for automated termination of laser-flux delivery to an eye, in the event that predetermined criteria of laser-flux distribution are not tolerably met.

The invention achieves the foregoing objects by subjecting a laser beam to certain shaping and homogenizing operations prior to any attempt to specially characterize the beam for a particular sculpturing surgical procedure. In a preferred embodiment, the shaping and homogenizing operations present a tolerably homogeneous beam of enlarged dimension, so that specialty-characterizing may proceed on a dimensional scale that is greater than the corresponding dimension of ultimate surgical delivery to the eye, thereby enabling greater control of the quality of specialty-characterizing. Provision is made for selectively monitoring the quality of the homogeneity and/or of the specially-characterized beam, with further provision for automated cutoff of laser beam delivery to an eye in the event that quality is not within predetermined limits of tolerance. And preferably, all beam shaping, homogenizing and characterizing operations proceed in a controlled environment which precludes ozone development and thus minimizes the beam-degrading effect o ozone and particulates or other contaminants.

DETAILED DESCRIPTION

The invention will be illustratively described for preferred and other embodiments, in conjunction with the accompanying drawings, in which:

FIG. 3a depicts beam-section area for a first condition in the apparatus of FIG. 1;

FIG. 3b depicts a horizontal beam-intensity profile for the condition of FIG. 3a;

FIG. 3c depicts a vertical beam-intensity profile for the condition of FIG. 3a;

FIG. 4a depicts a beam-section area for a second condition in the apparatus of FIG. 1;

FIG. 4b depicts a horizontal beam-intensity profile for the condition of FIG. 4a;

FIG. 4c depicts a vertical beam-intensity profile for the condition of FIG. 4a;

FIG. 5a depicts beam-section area for a third condition in the apparatus of FIG. 1;

FIG. 5b depicts a horizontal beam-intensity profile for the condition of FIG. 5a;

FIG. 5c depicts a vertical beam-intensity profile for the condition of FIG. 5a;

FIG. 6 is a graph of an optical-filter characteristic;

FIG. 7a depicts beam-section area for a fourth condition of FIG. 1;

FIG. 7b depicts a horizontal beam-intensity profile for the condition of FIG. 7a;

FIG. 7c depicts a vertical beam-intensity profile for the condition of FIG. 7a;

Figure 1:
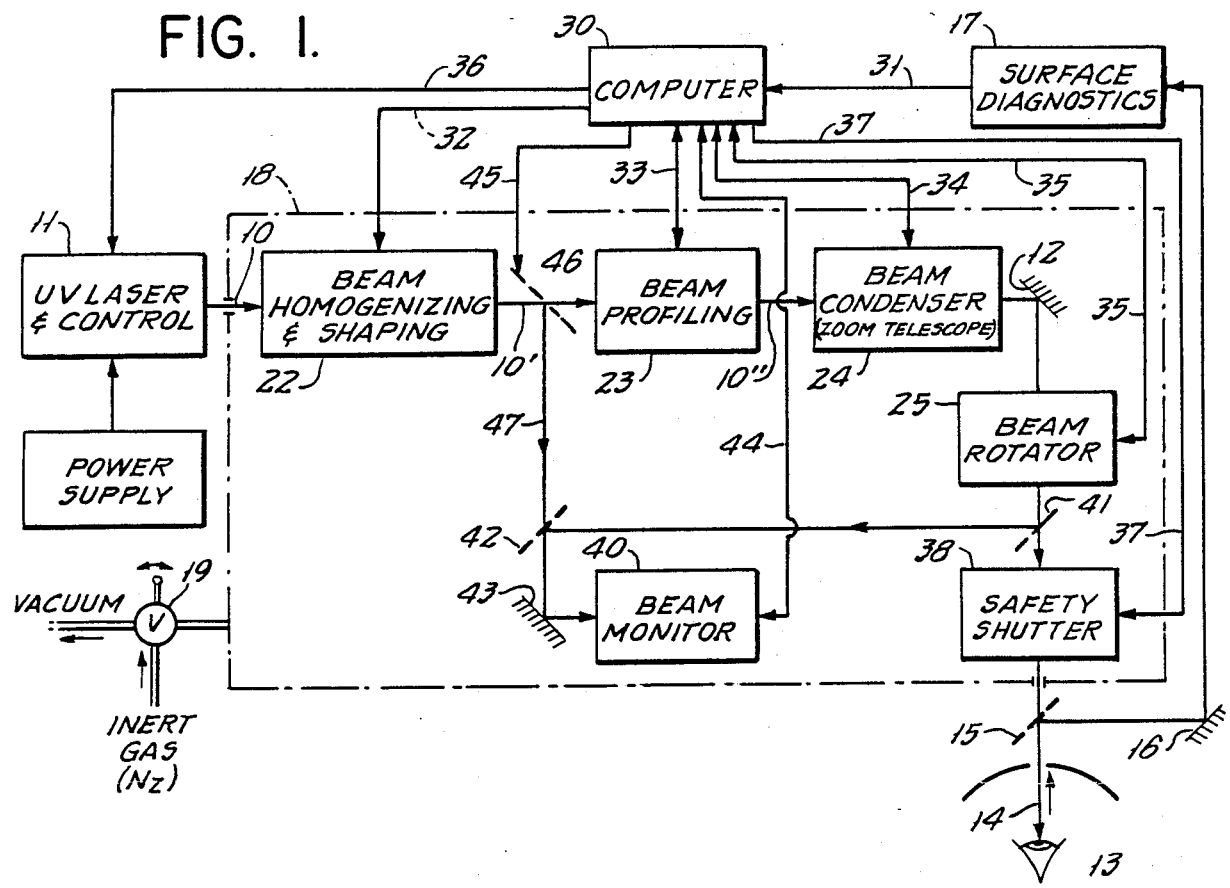
FIG. 1 is a simplified block diagram to show the functional relationship of generalized optical, mechanical and electrical components of apparatus incorporating the invention.

In FIG. 1, the invention is shown in conjunction with apparatus for delivery of the beam output 10 of an ultraviolet laser 11 along an optical path which is horizontal until folded at 12 for vertically downward fixed-axis passage to the eye 13 of a patient, it being understood that the patient may be suitably restrained, facing up, with the eye 13 also retained for coincidence of the visual axis with the axis 14 of impinging laser radiation. In preparation for laser surgery upon the anterior surface of eye 13, illuminating and reflecting components of a corneascope or other means of evaluating anterior topography of eye 13 will have been indexed into alignment with axis 14, as by mounting such components on an index arm which can be selectively swung into and out of topography-measuring position; in the drawing, these illuminating and reflecting components are collectively symbolized by folding mirrors 15-16, and camera and display components of the corneascope will be understood to be part of surface-diagnostic means 17.

The invention is primarily concerned with means for processing and monitoring the output beam 10, for assuring the safety and quality of the radiation delivered at 14 for operation on eye 13. And the optical means for such processing and monitoring are preferably contained within a sealed enclosure 18, whereby a suitably inert gas environment may assure against such beam-degradation as would occur from ozone development in an air environment; legends applied to the respective inlets of valve 19 suggest that the inert environment may be provided by a supply of dry nitrogen gas, following evacuation of air from enclosure 18.

One of the existing commercial ultraviolet-laser products of Questek Inc., Billerica, Massachusetts, for example their Model 2460 excimer laser operating with argon-fluoride, is satisfactory for use as laser 11. For this product, energy per pulse is selectively variable up to 275 millijoules, pulse width is in the range 8 to 20 nanoseconds, and pulse-repetition rate is selectively available up to 150 Hz, being typically and preferably in the range 5 to 15 Hz for presently described purposes; full rated power is not necessarily required by the invention, but this laser includes its own built-in microprocessor to control laser output power, gas filling and laser-system diagnostics, whereby predetermined output power can be automatically maintained for an extended useful life, as compared with other excimer lasers.

Laser 11 emits a collimated beam 10 of typical approximate sectional dimensions 22-mm by 7-mm, wherein the long dimension is horizontal and will be referred to as the width dimension (W) along the X axis, and the short dimension is vertical and will be referred to as the height dimension (H) along the Y axis. These dimensions are stated as approximate because, as indicated for the spatial (section) and width distribution views of FIGS. 3a and 3b, the generally rectangular emitted-beam section is characterized by laterally extending irregular fringes of greater relative intensity at both ends of the width dimension. These fringes are picked off by a scraper 20 (FIG. 2) for dissipation at a rap 21; scraper 20 has an elongate rectangular opening in its reflecting surface, whereby the scraped beam is characterized by the slightly reduced width W' for a more regular rectangular section area wherein the width (W') still greatly exceeds the height dimension H. As best seen in FIGS. 3b and 3c, the cross-sectional intensity profiles are different in the X and Y directions. In the X direction, the profile is essentially a "flat top", in that the higher end peaks have been discarded by the scraper; and in the Y direction, the intensity distribution is substantially Gaussian about the midpoint of the H dimension. For the dimensional legends applied to FIG. 3c, the scraper 20 will be seen to have selected that part of the Y-axis intensity distribution which exceeds half the maximum.

In accordance with a feature of the invention, the scraper 20 is but one of a succession of optical elements of first beam-processing mans 22, generally indicated in FIG. 1 as beam homogenizing and shaping means, the function of which is to preset at path location 10' an acceptably homogeneous collimated beam of circular section, wherein the cross-sectional distribution of flux density is relatively uniform and the circle diameter is considerably larger (e.g., 14-mm) than the maximum 5 to 7-mm diameter characterized beam ultimately delivered at 14 to the eye.

The large homogeneous circular beam 10' is then subjected to further processing at 23, for profiling purposes. This may involve applying characterized reflectance or filtering treatment to the beam, in accordance with teachings in said application Ser. No. 891,169, or it may involve applying a characterized succession of mask openings to control a particular succession of lapped areas of beam projection in the course of a given surgical procedure, in accordance with teachings in said application Ser. No. 891,285. After this second or profiling operation at 23, the beam at location 10" is fully characterized (whether by area distribution of intensity (I) or by time distribution of correlated lapping areas), but to a scale which is preferably in the order of at least twice the scale desired for eye delivery at 14. Third beam-processing means 24 which is labeled "beam condenser", but which will be understood to include a zoom telescope, should scale adjustability be desired, brings the characterized beam to the desired scale for surgical delivery at 14.

For those situations in which an astigmatic error is to be correctively improved, the characterization at 23 will be understood to be such as to develop characterizing symmetry on laterally opposite sides of a single diametric axis across the circle of the laser beam, and a beam rotator 25 is provided on the optical path prior to delivery via beam 14, to enable the surgeon to set the orientation axis of astigmatic-error correction, based on the presurgical diagnosis of the particular eye 13.

A computer 30 is shown with multiple storage and control capabilities, namely: with a connection 31 from the corneascope or other topographical instrumentation 17, for storage and evaluation purposes; control connections 32, 33, 34, 35 to different beam-processing and manipulating components of the system; control connection 36 to the laser 11; and a control connection 37 to one or more safety shutters, such as the shutter 38 shown just prior to exit of beam 14 from the environmental enclosure 18.

A beam monitor 40 is shown to be supplied, via beam-splitter pick-off at 41 and folding mirrors 42-43, with a fraction of the total beam that has been characterized and scaled down for surgical delivery. This fraction is for the total section of the beam but the picked off energy fraction is relatively small (e.g., 5 percent or less) of the energy content of the unsplit beam. Monitor 40 will be further described below, but it here suffices to state that it continuously observes the characterization of the delivered beam and, via a control and feedback bus 44, communicates with the computer. One or more criteria of beam character and quality in the monitoring sample are evaluated via the computer, and if predetermined tolerance criteria ar not met, the computer will not issue a shutter-opening command in control line 37 to the safety shutter 38. Finally, a computer control connection 45 is schematically indicated for concurrent bodily displacement of a beam-sampling splitter 46 into and out of the homogenized circular beam at 10', in coordination with in and out bodily displacement of the mirror 42 with respect to a split sample path 47 to the beam monitor 40, whereby, when desired, the beam at 10' can be verified for its adherence to tolerance limits, as a further precondition of beam characterization and delivery to the eye.

Returning to FIG. 2, beam-homogenizing and shaping means 22 is seen to include a beam-expanding pair of anamorphic elements 50-51, an optional spatial filter 52, a scraper 53 having an aperture configured to reduce the transmitted laser beam to a circular section (with deflection of the unused remainder of the beam to a trap 54), and an optical filter 55. More particularly, the anamorphic beam-expander elements 50-51 may be cylindrical lenses, or prisms (as shown), suitably of right-triangular section, with 45° corner angles. Prisms 50-51 are oriented to expand the H dimension to the extent of converting the rectangular-section beam of FIG. 3a to the square-section beam of FIG. 4a, i.e., wherein the expanded H dimension equals W'; the resultant beam-intensity profiles in the X and Y directions are schematically indicated in FIGS. 4b and 4c.

After expansion to square section, the beam may be passed through the spatial filter 52 which increases the uniformity of the respective dimensional-intensity profiles (FIGS. 4b and 4c) by focusing the beam through a small aperture or pinhole, thereby removing high spatial-frequency intensity variations. This spatial filter may comprise either image-forming mirrors or lenses, the latter being shown for schematic simplicity. At exit from spatial filter 52, the sectional dimensions of the beam are essentially as shown in FIG. 4a.

Having been scraped at 53 to a circular section, which is preferably substantially tangent to the respective sides of the square section (FIG. 4a), the beam is generally as displayed in FIGS. 5a, 5b, 5c, wherein the dimension W" is substantially the dimension W' of FIG. 4a. The beam next passes through optical filter 55, with spatially uniform transmission in the direction parallel to the X axis, and with non-uniform but axially symmetric transmission characteristics in the orthogonal direction (Y), see FIG. 6. The nonuniform transmission profile of FIG. 6 is that required to compensate for the truncated quasi-Gaussian profile the circle diameter is considerably larger (e.g., 14-mm) depicted in FIG. 5c, and the circular beam 10' which results from filter action at 55 has approximately uniform cross-sectional intensity in all directions, as shown schematically in FIGS. 7b and 7c, with a sectional diameter W" which is unchanged from that which is incident on filter 55. The beam 10' will thus be understood to have been homogenized, in terms of its flux-density (intensity) distribution, essentially throughout its full circular section, although the value of the intensity will have been attenuated inter alia by means 55 to a reduced magnitude I'.

It will be recalled that the scale of the section of beam 10' is large, e.g., 13 or 14-mm diameter, compared with the size, e.g., about 5-mm diameter, which may be prescribed for delivery at 14 to the eye 13. The lower half of FIG. 2 deals with specific illustrative components for specifically characterizing energy distribution across the beam and for reduction of the beam section area for such delivery at 14.

Figure 2:
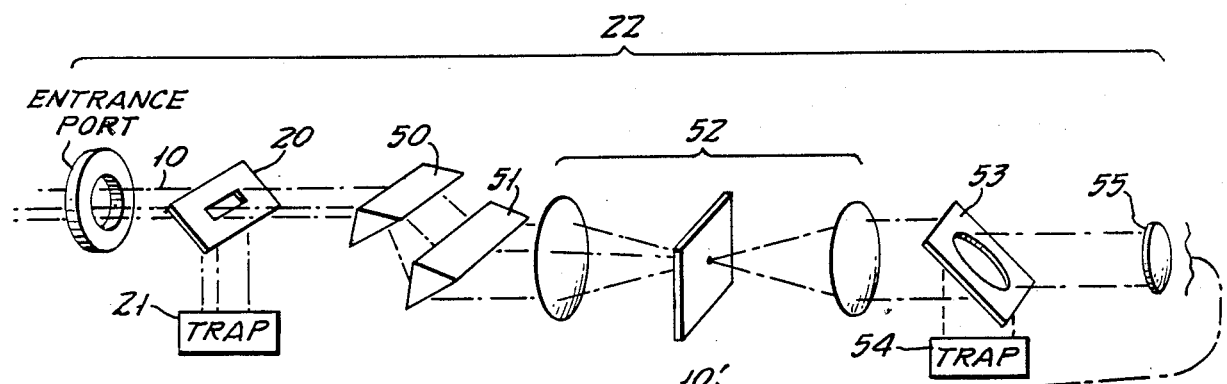
FIG. 2 is an expanded schematic diagram of some of the optical components of FIG. 1.

In the embodiment of FIG. 2, the characterizing of energy distribution across the laser-beam section is determined by filter means that is selectively positioned in the beam path, the particular selected filter being as appropriate for the corneal ablation prescribed by the ophthalmologist to correct refractive errors of the patient's eye. This technique is disclosed in greater detail in said pending application Ser. No. 891,285. Briefly, a selected characterizing filter A is one of a plurality (A to F) carried at equally spaced locations on a disc or turret 56 that is angularly indexable about a fixed axis 57; the diameter of filter openings at locations A to F may desirably be slightly less than that of the beam at 10', e.g., a 0.5-mm reduction in beam diameter, thus providing a tolerance for possible misalignment. Indexing rotation is imparted to disc 56 by drive means 58, in cooperation with the means symbolized at 59 for enabling precise location of each possible index position, it being understood that bus 33 of FIG. 1 laces the computer in the control loop which includes the drive and locating means 58-59.

Filter A may be characterized by a transmission profile which passes maximum beam intensity at the center and which progressively attenuates beam intensity as an increasing function of radius about the center; such a filter enables greatest depth of ablation at the center of beam 14, diminishing progressively to zero or substantially zero ablation at the circular periphery of the beam section. Such a characterizing filter at A will find utility in spherically sculpturing the cornea to greater radius of curvature, in corrective reduction of myopia.

In analogous manner, a characterizing filter at B may be designed to effect spherical corrective reduction of hyperopia, by passing greatest beam intensity at maximum radius of that circular area of the cornea which is to be optically improved; in this case, filter attenuation of the beam increases progressively with decreasing radius, thereby enabling beam 14 to reduce the radius of cornea curvature. In this particular case of hyperopia reduction, it is preferred that the opening at B shall be larger than that at other filer locations, i.e., that opening B shall not be operative to reduce the diameter of the homogenized beam, thus defining an annulus outside the optically corrected area; within this annulus, the attenuation characteristic of filter B preferably increases to maximum at the outer diameter, whereby sharp-edge development can be avoided in the sculptured surface and epithelium regrowth can proceed more rapidly.

In further analogous manner, a characterizing filter at C may be designed to effect a cylindrical curvature correction, as for corrective reduction of an astigmatic condition of eye 13. The filter at C may thus be characterized to transmit the cylindrical laser beam with greatest intensity along a diametric alignment through the center of the filter, and with a laterally symmetrical distribution of progressive beam attenuation which increases with lateral offset from the diametric alignment. The particular orientation of the thus-characterized beam is effected by beam rotator 25, which may be a refracting prism, such as a "Dove" or "Delta" prism, but which is shown as a so-called "K-mirror", mounted for rotation about the local axis of the characterized beam; the bus 35 of FIG. 1 will be understood to enable computer control of an edge drive 60, pursuant to angular-position sensing at 61, the same having been selected and set, for a given procedure, in accordance with requirements indicated by prior examination of eye 13.

In preparation of the cornea to receive a transplant, another of the opening locations (e.g., D) may be of diameter which, after reduction at 24, has been predetermined to create a sculpturing removal of corneal tissue to an extent suitable for receiving the transplant.

Remaining turret locations E and F may be equipped with further different filters, e.g., to achieve myopia correction or hyperopia correction via filter-density distributions which are specifically different from those at A and B. Or these positions may be equipped with filter spares, in the event of filter degradation at A or B, in the course of extended usage.

The safety shutter 38 is schematically shown for fail-safe operation, being a blade 62 pivoted o a fixed axis and continuously biased by a tension spring 63 toward its elevated position 62', in which beam 14 is cut off. It is only when an actuating solenoid 64 is actuated, by a command signal in line 37, that blade 62 can be displaced downward, to the position shown in solid outline, to allow beam 14 delivery to eye 13.

Figure 2A:
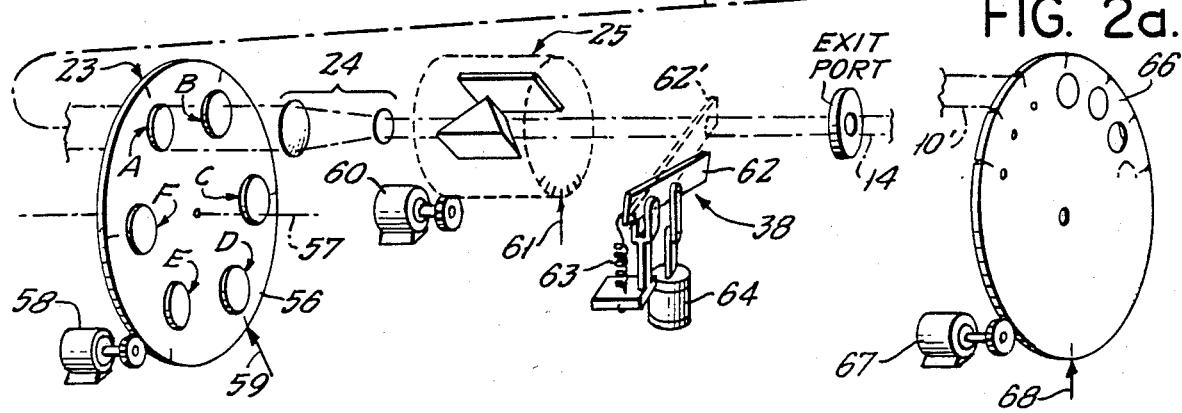
FIG. 2a is a fragmentary diagram to show an alternative for certain components of FIG. 2.

The fragmentary showing of FIG. 2a is merely illustrative of alternative use of the indexing-mask technique of said Serial No. 891,285, in place of the characterized-filter technique described in connection with disc 56 in FIG. 2. The disc 66 of FIG. 2a will be understood to have computer-coordinated drive at 67 pursuant to position-sensing at 68, to the end that computer-controlled successions of beam pulses will be limited by mask openings of progressively different size, from one to the next index location of disc 66. If these mask openings are circular and of progressively different radii, then the cumulative effect of an indexed succession of beam pulses will be in the direction of myopia correction. If these mask openings are elongate rectangular, with progressive variation in width and with the central longitudinal axis of symmetry consistently oriented (e.g., strictly radially) for all indexed positions, then the cumulative effect of an indexed succession of beam pulses will be in the direction of astigmatism correction, with the astigmatic-correction axis determined by preselected setting of image orientation, via means 25. Still further, hyperopia correction via the indexed-mask technique is achieved using successive annular mask openings wherein (a) the outer diameter is various throughout an annulus outside the diameter of the area of optical correction (to give a smooth contour out to the untreated radially outer region of the anterior surface) and wherein (b) the inner diameter is various throughout the area of optical correction.

Beam monitoring, alluded to at 40 in FIG. 1, will be discussed in greater detail in connection with FIG. 8, wherein the beam splitter 46 is seen to be pivotally mounted for movement between its normally retracted position (solid outline) and its selectively extendable position 46'. Mirror 42 is also mounted for limited pivotal movement from its reflecting position (shown) to a retracted position against a fixed stop 69, and a connecting link 70 (between crank arms associated with beam splitter 46 and with mirror 42) coordinates the described displacements, upon remotely controlled excitation of a single actuating means 71.

In the retracted position of splitter 46, the homogenized beam 10' is transmitted directly to means 23, 24 for beam profiling or such other characterizing as may be selected for beam (14) delivery, while a sample 72 of the characterized beam is reflected at 42 to the monitoring means 40; in the extended position (46') of beam splitter 46, a sample 73 of the homogenized beam 10' is directed to monitoring means 40, while the characterized-beam sample 72 is passed through an opening 42' of mirror 42, to a dissipation trap 74. Thus, for the described arrangement, the monitoring means 40 normally is continuously observing a sample of the characterized beam that is being delivered or is deliverable at 14, while sampling of the homogenized beam 10' is only selectively available for observation.

In a preferred employment, the monitoring means 40 comprises video-camera means that is sensitive to ultraviolet radiation emitted by the laser; illustratively, this is an Ultricon product of RCA, Model TC-2000, equipped with an ultraviolet-responsive photocathode, and it will be understood that the device 40 includes such beam-attenuating filter means as may be necessary to adapt sampled-beam intensity to the response range of the Ultricon. After digitizing at 75, one frame of the video-signal output of the Ultricon is stored by a frame-grabber 76, so that only digitized signals are conveyed by the bus (44) connection to the computer 30. Processing at the computer may be not only to determine whether one or more criteria have been satisfied but also to enable one or more displays of processed data. A printer 77 is shown connected for print-out of selected computer processed beam-intensity data, and means 78 may process the data for one or more types of display at 79; for example, the display at 79 may be an isometric display of intensity profiles, of a grabbed frame of the observed beam sample, the profiles being taken for X-axis line sweeps at successive increments of combined X-directed and Y-directed offset, from one to the next line sweep. Alternatively, and as suggested by concentric circles in the display 79 of the drawing, scanned variations in intensity may color-modulate the display, so that for a beam-characterization that is to effect a hyperopia correction, more closely adjacent concentric circles of particular different colors may indicate a desired or prescribed condition of sufficiently strong maximum intensity at maximum radius of the beam, with satisfactory progression of intensity reduction to minimum (i.e., corresponding to a predetermined ablation-threshold minimum) at the center of the monitored beam. Departures from norm criteria for a given radius of particular-color modulation can be visually monitored by viewing the display at 79, o may be evaluated by suitable processing at 30 to enable print-out of departure data at 77; and as long as such departures are within predetermined tolerance thresholds, a shutter-actuating signal can be supplied to shutter-control line 37 by a safety-signal generator 80.

It will be understood that the expression video-camera means at 40 is not limiting, but that other known techniques may alternatively be employed and are therefore within the meaning of said expression. For example, the video-camera means may comprise a luminescent plate which responds to incident ultraviolet radiation and which converts an ultraviolet image to a visible image, a video camera that is responsive to visible light being focused at the visible image.

Figure 8:
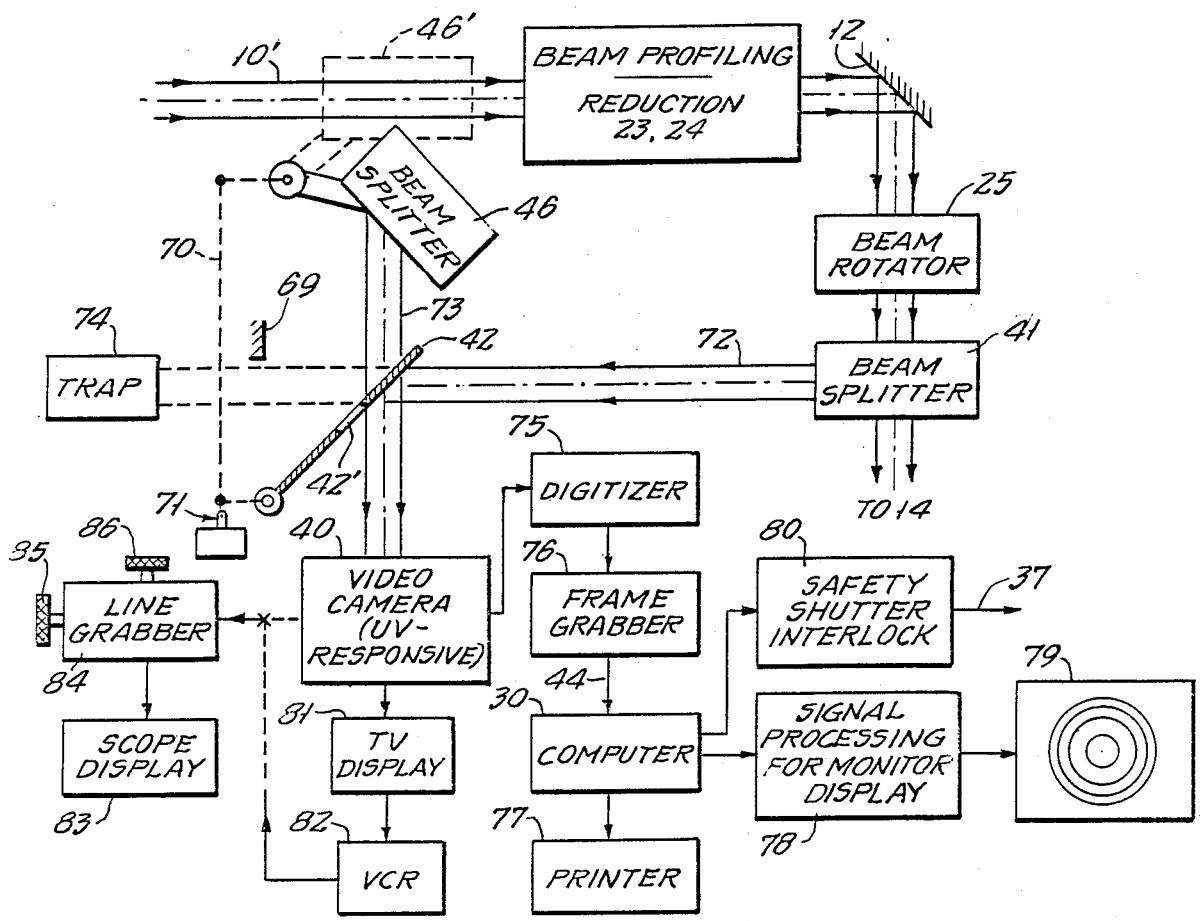
FIG. 8 is a fragmentary diagram schematically showing detail of beam-monitoring features of the invention.

FIG. 8 also shows use of the output of the video-camera means to generate an intensity-modulated or TV display 81 of the currently viewed beam section, with VCR (82) provision for storing of the sampled beam, e.g., at different observation times. Dashed-line connections will be understood to suggest an ability at 83 to display the VCR-recorded data for any given frame;

and, through the intermediary operation of a line grabber 84 with provision for independent X-line selection at 85 and independent Y-line selection at 86, the display at 83 may be either an X-line intensity profile across the observed beam, or a Y-line intensity profile. And in the event that it should be desire to rotate the diameter along which the beam-intensity profile is to be observed, a single setting of the X-line adjustment (85) to its centered position (Y=0) will serve, merely by controlled angular displacement of the beam rotator 25 about the local axis of the beam. Such rotation will be understood to have special utility, when a cylindrically characterized (astigmatism-correcting) intensity profile is to be observed; in this situation, means 25 is rotated until the centered X-line display (83) of intensity is flat for its X extent, whereupon a Y-line selection for display at different values of the X position will enable quick visual observation of whether the "cylindrical" intensity distribution is sufficiently symmetrical about the Y=0 point for all X values of the Y line selected at 86.

Figure 9:
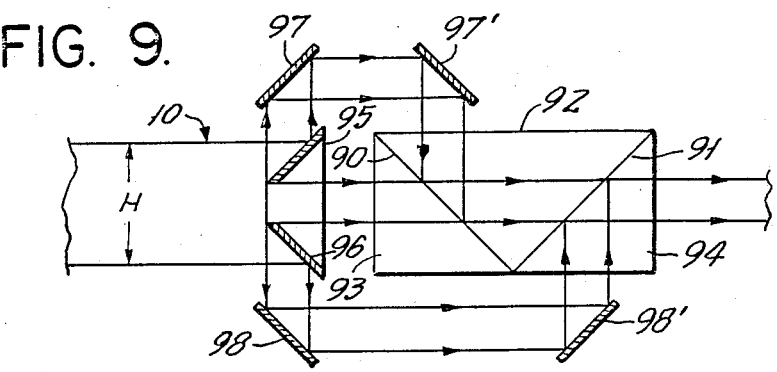
FIG. 9 is an optical diagram of component parts of an alternative for certain beam-homogenizing elements of FIG. 2.
Figure 10:
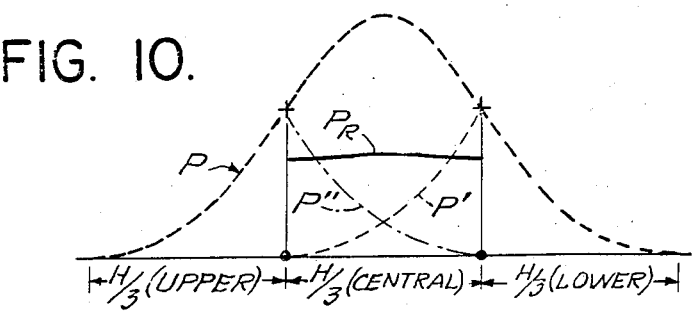
FIG. 10 is a graph which depicts the functional operation of the component parts of FIG. 9.

FIGS. 9 and 10 serve for illustration of another beam-folding homogenizing technique, generally as a replacement for the filtering device 55 (FIG. 6) and requiring less Y-axis limitation of the laser beam 10 than the I/2 intercepts depicted in FIG. 3c for the output of scraper 20. Thus, for purposes of discussion of FIGS. 9 and 10, the full H dimension of the vertically expanded laser beam 10″ which enters the folding device of FIG. 9 will be understood to be substantially greater than the W″ extent described and shown in connection with FIGS. 5a and 5c, this being among other things for the reason that the device of FIG. 9 is designed to accept a much greater spread of the quasi-Gaussian Y-axis distribution which characterizes the beam 10 output of laser 11.

More specifically, the folding device of FIG. 9 comprises firs and second beam-splitting interfaces 90-91 between a central triangular optical prism 92 and two smaller outer triangular prisms 93-94, plus an inlet assembly of spaced reflectors 5-96, and outer pairs of reflectors 97-97′ and 98-98′ which respectively serve folded components of the beam 10. The reflectors 95-96 each select an outer one-third fraction of the expanded height dimension H, diverting these fractions in opposite directions for further reflection by mirrors 97-98, parallel to but laterally offset from the longitudinal path of the remaining central one-third fraction. At the longitudinal location of the operative part of the beam splitter 90 which intercepts the central one-third fraction of the incoming beam 10, mirror 97′ is operative to deflect the divided upper one-third fraction into cumulatively additive relation with the central one-third fraction; similarly, at the longitudinal location of the operative part of the beam splitter 91 which intercepts the cumulatively added central and upper thirds of beam 10, mirror 98′ is operative to reflect the divided lower one-third fraction into cumulatively additive relation with the central one-third, and with the already added upper one-third fraction.

FIG. 10 graphically depicts the functional result of what has been described in connection with FIG. 9, the utilized height (H) of the laser beam 10 being so substantially greater (than that described in connection with FIG. 3c) as to comprehend most of the quasi-Gaussian intensity profile P of beam 10, the profile P being shown by heavy dashed lines. The upper third of this profile P is picked off and transmitted by mirrors 95-97-97′ for cumulative addition at 90 with the central third, the thus-displaced upper third being indicated by light-dashed line P′. Similarly, the lower third of this profile P is picked off and transmitted by mirrors 96-98-98′ for cumulative addition at 91 with the already-combined upper and central thirds. The net result is a beam output which has the H/3 dimension of the central one-third and which has a cumulatively added Y-axis intensity distribution substantially as indicated by the solid-line profile $P_R$. And it will be understood that anamorphic lens or prism treatment applied to this substantially flat-profile output beam may be employed (as described in connection with elements 50-51) to expand this H/3 dimension into conformance with the utilizable W′ dimension of the initially scraped laser beam.

The described invention will be seen to meet all stated objects and to provide the surgeon with a precision tool for enhanced quality and safety of corneal-sculpture procedures. Optical system components, including for example the anamorphic components 50-51 and the spatial-filter components, are available from various suppliers such as Melles Griot, and it is recommended that they be of vacuum ultraviolet-grade fused silica, preferably coated, as appropriate for the involved laserbeam wavelength.

It will be understood that, although the computer (30) operated means 77-78-79 is undoubtedly to b preferred for optimum safety and monitoring assurance, the described further monitoring means 81-82-83-84, in conjunction with selective manipulation of adjustable means 85-86 may alone provide sufficiently assuring monitoring functions to serve relatively simple and straightforward sculpting procedures.

It is to be understood that, for simplifying purposes, the surgical procedures which have been discussed have assumed that optical correction of a given eye involves only elimination or reduction of optical errors attributable to the topography of the cornea, thus avoiding discussion of such further optical errors as may be contributed by the inner natural lens of a given eye. It will be understood, therefore, that the corneal topography data ascertained at 17 is to be taken in context with data from prior examination of the eye's overall performance. From such examination, the extent of required correction is ascertained; corneal-sculpting procedure commences with the measured topography data as a starting point, and must follow such a prescribed combination of spherical and/or cylindrical ablative procedures as will best serve, through sculpted modification of corneal topography, as to tolerably achieve the desired overall correction of the eye's performance.

While the invention has been described for preferred embodiments and techniques, it will be understood that modifications ma be made without departing from the scope of the invention. For example, if the filter 55 of FIG. 2 is omitted, the quasi-Gaussian distribution of FIG. 5c will be seen to approximate that which can serve the cylindrical flattening result for reduction of an astigmatism; and to achieve this result with the apparatus of FIG. 2, one need only (a) omit a characterizing filter at one of the indexible openings (e.g., F) of turret 56, thereby relaying beam 10′ direct to condenser 24 and to beam rotator 25, and (b) adjust the latter to an angular position at which the quasi-Gaussian distribution is across a diametric orientation appropriate to the astigmatism which is to be corrected.

Further by way of example, and again if the filter 55 of FIG. 2 is omitted, and for a limited range of cases requiring myopia correction, the quasi-Gaussian distribution of FIG. 5c will be seen to approximate that which can serve the necessary spherical flattening result; to achieve this result with the apparatus of FIG. 2, one need only (a) omit a characterizing filter at one of the indexible openings of turret 56, thereby relaying beam 10' directly to condenser 24 and to beam rotator 25, and (b) continuously rotate the later for a given number of half turns in the course of a given treatment. In this myopia-correcting situation, it will be seen to be possible to extend the limited range of myopia correction, through a controlled expansion of the H distribution of flux-density distribution, as from the pronounced curvature of FIG. 3c to the less pronounced curvature of FIG. 4c; beam rotation in the course of a given treatment at less pronounced curvature (FIG. 4c) will effect a lesser-diopter change than will beam rotation at the more pronounced curvature (FIG. 3c). And selective variation of the particular curvature (e.g., between or beyond those of FIGS. 3c and 4c) will be seen to be available as by selective relative rotation of anamorphic means 50-51 about axes transverse to the laser-beam and parallel to the longitudinal axes of these prisms.

Still further by way of example, and for cases in which both myopia and astigmatism correction are to be achieved, the above-discussed quasi-Gaussian distribution can be used to accomplish both of these kinds of correction in a given treatment, by suitably programming the rate of image rotation as a function of azimuth for each rotation; the nature of such programming will be understood to be such as to produce greatest integrated exposure along the meridian requiring astigmatic correction while producing, for the same treatment, sufficient integrated exposure via the Gaussian distribution for all azimuth orientations to achieve the desired component of myopia correction. Stated in other words, the varying rate of rotation of the Gaussian-characterized beam should be such as to spend more time along the astigmatism axis, as compared with less time along the axis perpendicular to the astigmatism axis, in order to achieve combined astigmatism and myopia correction.

What is claimed is:

1. Apparatus for performing an ablating sculpture of the anterior surface of the cornea of an eye, comprising an excimer laser for pulsed emission of ultraviolet radiation in a beam of rectangular section wherein intensity distribution is generally uniform in the longer-dimensional direction and is generally Gaussian about the center of its shorter-dimensional direction; and optical elements in a path of beam transmission to the eye, including means for centering the beam on the viewing axis of the eye and for shaping the beam to a circle wherein said generally Gaussian distribution is symmetrical about a diameter of the circle and wherein the diameter of the circle conforms to that of the area of the cornea to be subjected to ablation; said optical elements including beam-rotating means, whereby the orientation of the Gaussian distribution may be subjected to rotation with respect to the eye.

2. Apparatus according to claim 1, in which said beam-rotating means includes provision for selective rotational adjustment and setting of the orientation of the Gaussian distribution, whereby an astigmatism-correcting change of cornea curvature may be effected for a given laser-beam exposure to the eye.

3. Apparatus according to claim 1, in which said beam-rotating means includes provision for continuously driven rotation in the course of a given laser-beam exposure o the eye, whereby for beam rotation of at least 180 degrees at the eye and for the direction of a given laser-beam exposure to the eye, a myopia-reducing change of cornea curvature may be effected.

4. Apparatus according to claim 1, in which said beam-rotating means includes provision for beam rotation in the course of a given laser exposure to the eye, the rate of rotation being a function of angular orientation of the Gaussian distribution, such that more time is spent at the orientation identifiable with an astigmatism to be corrected, as compared with less time spent at the orientation perpendicular to the astigmatism axis.

5. In apparatus using an ultraviolet laser to correct an optically deficient eye by volumetric ablative removal of corneal tissue from the anterior surface and with penetration of the stroma, wherein laser-beam delivery is on an optical path which terminates with a fixed cornea-impingement axis aligned with the axis of the eye, and wherein beam-characterizing means so characterizes intensity distribution within a predetermined circle of laser-radiation exposure to the cornea as in the course of a predetermined exposure time to so distribute the cumulative depth of ablation as to achieve a new and improved corneal curvature, the improvement wherein the laser is an excimer laser and wherein beam-homogenizing means for effecting a relatively uniform cross-sectional distribution of flux density is on said path downstream from the laser and upstream with respect to the characterizing of intensity distribution, said beam-homogenizing means comprising scraper means limiting beam margins to a rectangular section (a) which is elongate in one dimension and which is of substantially uniform intensity profile along said one dimension and (b) which is relatively narrow in the other dimension and which is within a substantially 2:1 range of dimensional intensity-profile variation along said other dimension, and refractive anamorphic beam-expansion means oriented to expand said relatively narrow dimension to substantially the extent of said one dimension.

6. In apparatus using an ultraviolet laser to correct an optically deficient eye by volumetric ablative removal of corneal tissue from the anterior surface and with penetration of the stroma, wherein laser-beam delivery is on an optical path which terminates with a fixed cornea-impingement axis aligned with the axis of the eye, and wherein beam-characterizing means so characterizes intensity distribution within a predetermined circle of laser-radiation exposure to the cornea as in the course of a predetermined exposure time to so distribute the cumulative depth of ablation as to achieve a new and improved corneal curvature, the improvement in which the laser is an excimer laser producing an output beam of generally rectangular section wherein intensity distribution is generally uniform along an elongate first dimension and is characterized by generally Gaussian distribution along a second dimension transverse to said first dimension, beam-processing means including one or more optical elements on said path, said one or more optical elements being operative (a) substantially only along said second dimension of the beam section and (b) to expand said second dimension for substantial equality with said first dimension.

7. The improved apparatus of claim 6, in which said one or more elements includes refractive anamorphic beam-expansion means oriented to expand said second dimension to substantial equality with said first dimension.

8. The apparatus of claim 6, in which said beam-processing means includes scraper means limiting the beam to a circular section following beam-expansion.

9. The improved apparatus of claim 6, in which the height and width dimensions of the expanded beam are substantially greater than the beam-section dimensions at delivery to the eye, means for characterizing the flux distribution on the scale of said greater dimensions, and beam-condenser means operative to reduce the characterized beam to said predetermined circle.

10. The improved apparatus of claim 9, in which said beam-condenser means is a zoom telescope.

11. The improved apparatus of claim 6, in which a multiple-station turret mounts a plurality of different flux-distribution filters at each of a succession of stations that are individually and selectively indexible into said path following beam-expansion, and a beam-condenser downstream from said turret.

12. The improved apparatus of claim 6, in which an indexible turret is characterized by a successive plurality of openings at predetermined angular spacing, said openings being characterized by progressively changing beam-scraping radius about said path when each opening is indexed into position centered on said path.

13. The improvement of claim 6, in which said beam-processing means is contained in an enclosure having a beam-entry port proximal to beam exit from the laser and a beam-exit port proximal to the location of characterized beam delivery to the eye.

14. The improvement of claim 13, in which said enclosure is an environmentally sealed enclosure.

15. The improvement of claim 13, in which said enclosure has an environmental filling of a gas inert to laser radiation.

16. The improvement of claim 15, in which said gas is dry nitrogen.

17. The improved apparatus according to claim 6, in which the range of intensity-profile variation along the height dimension is in the range 2:1 or less.

18. In apparatus using an ultraviolet excimer laser to correct an optically deficient eye by volumetric ablative removal of corneal tissue from the anterior surface and with penetration of the stroma, wherein laser-beam delivery is on an optical path which terminates with a fixed cornea-impingement axis aligned with the axis of the eye, wherein beam-characterizing means so characterizes intensity distribution within a predetermined circle of laser-radiation exposure to the cornea as in the course of a predetermined exposure time to so distribute the cumulative depth of ablation to achieve a new and improved corneal curvature, and wherein beam-homogenizing means for effecting a relatively uniform cross-sectional distribution of flux density is interposed between the laser and said beam-characterizing means, the improvement in which computer means includes digitally stored tolerance data reflecting a predetermined level of uniformly distributed laser-beam intensity distribution across the beam prior to characterization of intensity distribution, and in which beam-monitoring means associated with said computer means includes a beam-sampling splitter positioned in said path prior to characterization of intensity distribution, said beam-monitoring means being electrically responsive to intensity distribution across the sampling beam and producing a digital output indicative of such distribution, said computer means indicating the beam-sampled distribution in relation to the digitally stored tolerance data.

19. The apparatus of claim 18, in which shutter means on said path and downstream from said splitter is normally closed to foreclose delivery of laser radiation to the eye, said shutter means having an actuating connection from said computer means and being actuable to open condition only in the event that the monitored distribution data conforms with the digitally stored tolerance data.

20. The improved apparatus of claim 18, in which said beam-processing means includes spatial-filter means following beam-expansion, for removing high spatial-frequency intensity variations from the beam.

21. In apparatus using an ultraviolet laser to correct an optically deficient eye by volumetric ablative removal of corneal tissue from the anterior surface and with penetration of the stroma, wherein laser-beam delivery is on an optical path which terminates with a fixed cornea-impingement axis aligned with the axis of the eye, and wherein flux distribution is so characterized within a predetermined circle of laser-radiation exposure to the cornea as in the course of a predetermined exposure time to so vary with time the intensity distribution across the beam so as to distribute the cumulative depth of ablation and thereby achieve a new and improved corneal curvature, the improvement in which computer means include a digital storage of a time-varying intensity distribution function across the beam that is predetermined to effect a selected curvature correction, and in which beam-monitoring means associated with said computer means includes a beam-sampling splitter positioned in said optical path after characterization of intensity distribution, said beam-monitoring means being electrically responsive to the time-varying intensity distribution in the sampling beam and producing a digital output that is indicative of the sampled distribution, said computer means indicating the beam-sampled distribution in relation to the digitally stored distribution data.

22. The improved apparatus of claim 21, in which the shutter means on said path and in downstream proximity to said splitter is normally closed to foreclose delivery of laser radiation to the eye, said shutter means having an actuating connection from said monitoring means and being actuable to open condition only in the event that the monitored distribution data and the digitally stored distribution data conform within predetermined tolerance limits.

23. The improved apparatus of claim 21, in which said beam-monitoring means includes a second beam-sampling splitter positioned in said path prior to time-varying characterization of the intensity distribution function, whereby homogeneity of the beam may be monitored prior to beam-characterizing.

24. The apparatus of claim 21, in which the characterizing of intensity distribution is a time-varying function of radius about the cornea-impingement axis.

25. The apparatus of claim 21, in which the characterizing of intensity distribution is a symmetrical function on laterally opposed sides of a diametrically extending axis intersecting the cornea-impingement axis, and selectively operable beam-rotation means for setting an angular orientation of the characterized beam consistent with the axis of an astigmatism to be reduced.

26. The apparatus of claim 25, in which said beam-rotating means is upstream with respect to said beam-sampling splitter.

* * * * *